US005698444A

United States Patent [19]
Baez et al.

[11] Patent Number: 5,698,444
[45] Date of Patent: Dec. 16, 1997

[54] SEROTONIN RECEPTOR PROTEIN AND RELATED NUCLEIC ACID COMPOUNDS

[75] Inventors: Melvyn Baez; Jonathan D. Kursar, both of Indianapolis, Ind.

[73] Assignee: Eli Lilly and Company, Indianapolis, Ind.

[21] Appl. No.: 173,436

[22] Filed: Dec. 23, 1993

[51] Int. Cl.⁶ .................................................. C12N 15/12
[52] U.S. Cl. .................. 435/325; 536/23.5; 435/252.33; 435/320.1
[58] Field of Search .......................... 435/6, 69.1, 240.2, 435/252.33, 320.1, 325; 536/23.5, 24.3, 24.31, 24.33

[56] References Cited

U.S. PATENT DOCUMENTS 4,992,373  2/1991  Bang et al. ........................... 435/69.6

FOREIGN PATENT DOCUMENTS 0565370  10/1993  European Pat. Off. .

OTHER PUBLICATIONS

Loric, S. et al., *FEBS Letters*, 312(2,3): 203–207, 1992.
Foguet, et al., *The EMBO Journal*, vol. 11, No. 9, pp. 3481–3487, 1992.
Foguet, et al., *Molecular Neuroscience*, NeuroReport 3, 345–348, 1992.
Kursar, et al., *Molecular Pharmacology*, vol. 42, pp. 549–557, 1992.
Wainscott, et al., *Molecular Pharmacology*, vol. 43, pp. 419–426, 1992.
Schmuck, et al., *FEBS Lett.*, vol. 342, pp. 85–90, 1994.
Choi, et al., *FEBS Lett.*, vol. 352, pp. 393–399.
Bonhaus, et al., *British Journal of Pharmacology*, vol. 115, pp. 622–628, 1995.

*Primary Examiner*—Marianne P. Allen
*Attorney, Agent, or Firm*—Thomas D. Webster; Paul J. Gaylo; David E. Boone

[57] ABSTRACT

This invention describes a novel human serotonin receptor, designated 5-HT$_{2F}$. This invention also encompasses nucleic acids encoding this receptor, or a fragment thereof, as well as methods employing this receptor and the nucleic acid compounds.

14 Claims, 2 Drawing Sheets

SEROTONIN RECEPTOR PROTEIN AND RELATED NUCLEIC ACID COMPOUNDS

BACKGROUND OF THE INVENTION

Since the discovery of serotonin (5-hydroxytryptamine, 5-HT) over four decades ago, the cumulative results of many diverse studies have indicated that serotonin plays a significant role in the functioning of the mammalian body, both in the central nervous system and in peripheral systems as well. Morphological studies of the central nervous system have shown that serotonergic neurons, which originate in the brain stem, form a very diffuse system that projects to most areas of the brain and spinal cord. R. A. O'Brien, *Serotonin in Mental Abnormalities*, 1:41 (1978); H. W. M. Steinbusch, "Handbook of Chemical Neuroanatomy", Volume 3, Part II, 68 (1984); N. E. Anden, et al., *Acta Physiologica Scandinavia*, 67:313 (1966). These studies have been complemented by biochemical evidence that indicates large concentrations of 5-HT exists in the brain and spinal cord. H. W. M. Steinbusch, supra.

With such a diffuse system, it is not surprising that 5-HT has been implicated as being involved in the expression of a number of behaviors, physiological responses, and diseases which originate in the central nervous system. These include such diverse areas as sleeping, eating, perceiving pain, controlling body temperature, controlling blood pressure, depression, schizophrenia, and other bodily states. R. W. Fuller, "Biology of Serotonergic Transmission", 21 (1982); D. J. Boullin, "Serotonin in Mental Abnormalities" 1:316 (1978); J. Barchas, et al., *Serotonin and Behavior*, (1973).

Serotonin plays an important role in peripheral systems as well. For example, approximately 90% of the body's serotonin is found in the gastrointestinal system, and serotonin has been found to mediate a variety of contractile, secretory, and electrophysiologic effects in this system. Another example of a peripheral network that is very sensitive to serotonin is the cardiovascular system, which also contains its own source of serotonin, i.e., the platelet. Given the broad distribution of serotonin within the body, it is understandable that tremendous interest in drugs that affect serotonergic systems exists. In particular, receptor-specific agonists and antagonists are of interest for the treatment of a wide range of disorders, including anxiety, depression, hypertension, migraine, compulsive disorders, schizophhrenia, autism, neurodegenerative disorders, such as Alzheimer's disease, Parkinsonism, and Huntington's chorea, and cancer chemotherapy-induced vomiting. M. D. Gershon, et al., "The Peripheral Actions of 5-Hydroxytryptamine", 246 (1989); P. R. Saxena, et al., *Journal of Cardiovascular Pharmacology*, 15:Supplement 7 (1990).

Serotonin produces its effects on cellular physiology by binding to specialized receptors on the cell surface. It is now recognized that multiple types of receptors exist for all neurotransmitters and hormones, including serotonin. The existence of multiple, structurally distinct serotonin receptors has provided the possibility that subtype-selective pharmacologic agents can be produced. The development of such compounds could result in new and increasingly selective therapeutic agents with fewer side effects, since individual receptor subtypes may function to affect specific actions of the different parts of the central peripheral serotonergic systems.

An example of such specificity can be demonstrated by using the vascular system as an example. In certain blood vessels, stimulation of 5-HT$_1$-like receptors on the endothelial cells produces vasodilation while stimulation of 5-HT$_2$ receptors on the smooth muscle cells produces vasoconstriction. Currently, the major classes of serotonin receptors (5-HT$_1$, 5-HT$_2$, 5-HT$_3$, 5-HT$_4$, 5-HT$_5$, 5-HT$_6$, and 5-HT$_7$) contain some fourteen to eighteen separate receptors that have been formally classified based on their pharmacological or structural differences. [For an excellent review of the pharmacological effects and clinical implications of the various 5-HT receptor types, see Glennon, et al., *Neuroscience and Behavioral Reviews*, 14:35 (1990).]

The present invention provides an additional human 5-HT receptor, designated 5-HT$_{2B}$, to those previously known. The characterization and treatment of physiological disorders is hereby furthered.

SUMMARY OF THE INVENTION

The present invention provides an isolated amino acid compound which comprises the amino acid sequence Met Ala Leu Ser Tyr Arg Val Ser Glu Leu Gln Ser Thr Ile
1           5                   10
Pro Glu His Ile Leu Gln Ser Thr Phe Val His Val Ile Ser
15              20                  25
Ser Asn Trp Ser Gly Leu Gln Thr Glu Ser Ile Pro Glu Glu
    30              35                  40
Met Lys Gln Ile Val Glu Gln Gly Asn Lys Leu His Trp
        45              50                  55
Ala Ala Leu Leu Ile Leu Met Val Ile Ile Pro Thr Ile Gly
            60              65                  70
Gly Asn Thr Leu Val Ile Leu Ala Val Ser Leu Glu Lys Lys
                75              80
Leu Gln Tyr Ala Thr Asn Tyr Phe Leu Met Ser Leu Ala Val
85              90                  95
Ala Asp Leu Leu Val Gly Leu Phe Val Met Pro Ile Ala Leu
    100             105                 110
Leu Thr Ile Met Phe Glu Ala Met Trp Pro Leu Pro Leu Val
        115             120                 125
Leu Cys Pro Ala Trp Leu Phe Leu Asp Val Leu Phe Ser Thr
            130             135                 140
Ala Ser Ile Met His Leu Cys Ala Ile Ser Val Asp Arg Tyr
                145                 150
Ile Ala Ile Lys Lys Pro Ile Gln Ala Asn Gln Tyr Asn Ser
155             160                 165
Arg Ala Thr Ala Phe Ile Lys Ile Thr Val Val Trp Leu Ile
    170             175                 180
Ser Ile Gly Ile Ala Ile Pro Val Pro Ile Lys Gly Ile Glu
        185             190                 195
Thr Asp Val Asp Asn Pro Asn Asn Ile Thr Cys Val Leu Thr
            200             205                 210
Lys Glu Arg Phe Gly Asp Phe Met Leu Phe Gly Ser Leu Ala
                215                 220
Ala Phe Phe Thr Pro Leu Ala Ile Met Ile Val Thr Tyr Phe
225             230                 235
Leu Thr Ile His Ala Leu Gln Lys Lys Ala Tyr Leu Val Lys
    240             245                 250
Asn Lys Pro Pro Gln Arg Leu Thr Trp Leu Thr Val Ser Thr
        255             260                 265
Val Phe Gln Arg Asp Glu Thr Pro Cys Ser Ser Pro Glu Lys
            270             275                 280

-continued

Val Ala Met Leu Asp Gly Ser Arg Lys Asp Lys Ala Leu Pro
            285                 290

Asn Ser Gly Asp Glu Thr Leu Met Arg Arg Thr Ser Thr Ile
295             300              305

Gly Lys Lys Ser Val Gln Thr Ile Ser Asn Glu Gln Arg Ala
310              315                 320

Ser Lys Val Leu Gly Ile Val Phe Phe Leu Phe Leu Leu Met
    325              330              335

Trp Cys Pro Phe Phe Ile Thr Asn Ile Thr Leu Val Leu Cys
            340          345              350

Asp Ser Cys Asn Gln Thr Thr Leu Gln Met Leu Leu Glu Ile
                355              360

Phe Val Trp Ile Gly Tyr Val Ser Ser Gly Val Asn Pro Leu
365              370              375

Val Tyr Thr Leu Phe Asn Lys Thr Phe Arg Asp Ala Phe Gly
    380              385              390

Arg Tyr Ile Thr Cys Asn Tyr Arg Ala Thr Lys Ser Val Lys
        395          400              405

Thr Leu Arg Lys Arg Ser Ser Lys Ile Tyr Phe Arg Asn Pro
            410              415              420

Met Ala Glu Asn Ser Lys Phe Phe Lys Lys His Gly Ile Arg
                425              430

Asn Gly Ile Asn Pro Ala Met Tyr Gln Ser Pro Met Arg Leu
435              440              445

Arg Ser Ser Thr Ile Gln Ser Ser Ser Ile Ile Leu Leu Asp
    450              455              460

Thr Leu Leu Leu Thr Glu Asn Glu Gly Asp Lys Thr Glu Glu
        465              470              475

-continued

Gln Val Ser Tyr Val
                480 hereinafter designated as SEQ ID NO:2.

The invention also provides an isolated nucleic acid compound that comprises a nucleic acid sequence which encodes for the amino acid compounds provided. Particularly this invention provides the isolated nucleic acid compound having the sequence

| | |
|---|---|
| ATGGCTCTCTCTTACAGAGTGTCTGAACTTCAAAGCACAATTCCTGAGCA | 50 |
| CATTTTGCAGAGCACCTTTGTTCACGTTATCTCTTCTAACTGGTCTGGAT | 100 |
| TACAGACAGAATCAATACCAGAGGAAATGAAACAGATTGTTGAGGAACAG | 150 |
| GGAAATAAACTGCACTGGGCAGCTCTTCTGATACTCATGGTGATAATACC | 200 |
| CACAATTGGTGGAAATACCCTTGTTATTCTGGCTGTTTCACTGGAGAAGA | 250 |
| AGCTGCAGTATGCTACTAATTACTTTCTAATGTCCTTGGCCGGTGGCTGAT | 300 |
| TTGCTGGTTGGATTGTTTGTGATGCCAATTGCCCTCTTGACAATAATGTT | 350 |
| TGAGGCTATGTGGCCCCTCCCACTTGTTCTATGTCCTGCCTGGTTATTTC | 400 |
| TTGACGTTCTCTTTTCAACCGCATCCATCATGCATCTCTGTGCCATTTCA | 450 |
| GTGGATCGTTACATAGCCATCAAAAAGCCAATCCAGGCCAATCAATATAA | 500 |
| CTCACGGGCTACAGCATTCATCAAGATTACAGTGGTGTGGTTAATTTCAA | 550 |
| TAGGCATTGCCATTCCAGTCCCTATTAAAGGGATAGAGACTGATGTGGAC | 600 |
| AACCCAAACAATATCACTTGTGTGCTGACAAAGGAACGTTTTGGCGATTT | 650 |
| CATGCTCTTTGGCTCACTGGCTGCCTTCTTCACACCTCTTGCAATTATGA | 700 |
| TTGTCACCTACTTTCTCACTATCCATGCTTTACAGAAGAAGGCTTACTTA | 750 |
| GTCAAAAACAAGCCACCTCAACGCCTAACATGGTTGACTGTGTCTACAGT | 800 |
| TTTCCAAAGGGATGAAACACCTTGCTCGTCACCGGAAAAGGTGGCAATGC | 850 |
| TGGATGGTTCTCGAAAGGACAAGGCTCTGCCCAACTCAGGTGATGAAACA | 900 |
| CTTATGCGAAGAACATCCACAATTGGGAAAAAGTCAGTGCAGACCATTTC | 950 |
| CAACGAACAGAGAGCCTCAAAGGTCCTAGGGATTGTGTTTTTCCTCTTTT | 1000 |
| TGCTTATGTGGTGTCCCTTCTTTATTACAAATATAACTTTAGTTTTATGT | 1050 |
| GATTCCTGTAACCAAACTACTCTCCAAATGCTCCTGGAGATATTTGTGTG | 1100 |
| GATAGGCTATGTTTCCTCAGGAGTGAATCCTTTGGTCTACACCCTCTTCA | 1150 |
| ATAAGACATTTCGGGATGCATTTGGCCGATATATCACCTGCAATTACCGG | 1200 |
| GCCACAAAGTCAGTAAAAACTCTCAGAAAACGCTCCAGTAAGATCTACTT | 1250 |
| CCGGAATCCAATGGCAGAGAACTCTAAGTTTTTCAAGAAACATGGAATTC | 1300 |
| GAAATGGGATTAACCCTGCCATGTACCAGAGTCCAATGAGGCTCCGAAGT | 1350 |
| TCAACCATTCAGTCTTCATCAATCATTCTACTAGATACGCTTCTCCTCAC | 1400 |
| TGAAAATGAAGGTGACAAAACTGAAGAGCAAGTTAGTTATGTATAG | 1446 | hereinafter referred to as SEQ ID NO:1.

This invention also provides recombinant nucleic acid vectors comprising nucleic acids encoding SEQ ID NO:2. This invention also encompasses recombinant DNA vectors which comprise the isolated DNA sequence which is SEQ ID NO:1.

The present invention also provides assays for determining the efficacy and adverse reaction profile of agents useful in the treatment or prevention of disorders associated with an excess or deficiency in the amount of serotonin present.

DETAILED DESCRIPTION AND PREFERRED EMBODIMENTS

Figure 1:
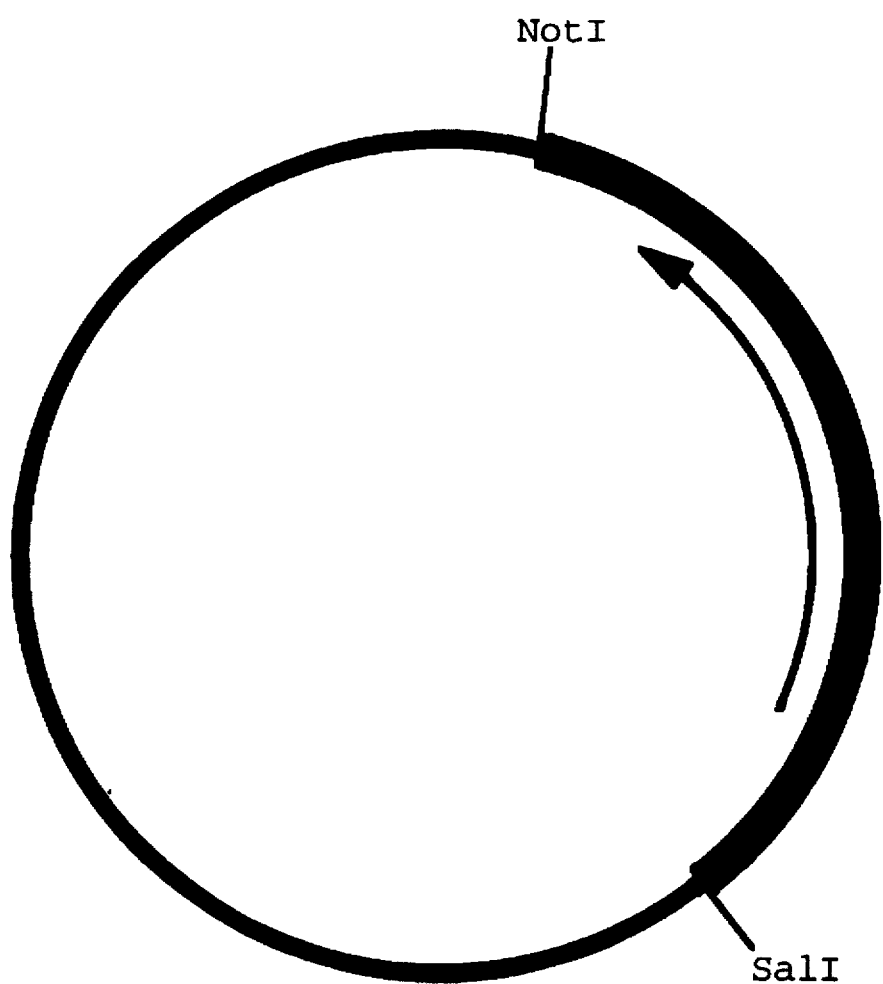
FIG. 1 is a restriction and function map of the plasmid pHu5HT$_{2B}$. The arc having the wider line indicates that protion of the plasmid which corresponds to SEQ ID NO:4, infra. The arrow delineates that region of the insert which encodes for the protein of SEQ ID NO:2 with the direction of the arrow indicating the natural order of transcription from the 5' end to the 3' end.

The terms and abbreviations used in this document have their normal meanings unless otherwise designated. For example "°C." refers to degrees Celsius; "N" refers to normal or normality; "mmole" refers to millimole or millimoles; "g" refers to gram or grams; "ml" means milliliter or milliliters; "M" refers to molar or molarity; "µg" refers to microgram or micrograms; and "µl" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the ribonucleosides uracil, cytidine, guanine, and thymine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments (T. Maniatis, et al., supra., p. 146). Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., "Molecular Cloning: A Laboratory Manual" (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid affinity for other nucleic acid. (See the definition of "hybridization", supra.)

The term "PCR" as used herein refers to the widely-known polymerase chain reaction employing a thermally-stable polymerase.

This invention provides the protein of SEQ ID NO:2, a human serotonin receptor, designated as a 5-$HT_{2B}$ receptor using the recently modified nomenclature system described in E. Zifa and G. Fillion, *Pharmacological Reviews*, 44:401–458 (1992). This receptor is found in a large number of tissues throughout the body, including adipose, adrenal, aorta, heart, kidney, liver, lung, mammary gland, ovary, pancreas, placenta, prostate, retina, salivary glands, skeletal muscle, small intestine, spinal cord, spleen, testis, thymus, thyroid, trachea, and uterus, as well as the amygdala, caudate, cerebral cortex, cerebellum, corpus callosum, hypotahalamus, pituitary, substansia nigra, subthalamic nucleus, and thalamus regions of the brain. This receptor is believed to potentiate both peripheral and central nervous system responses and is, therefore, an important target for pharmaceutical purposes.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, herein incorporated by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl
Asp, cyclohexyl
Glu, cyclohexyl
Ser, Benzyl
Thr, Benzyl
Tyr, 4-bromo carbobenzoxy Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% metacresol. Cleavage of the side chain protecting group(s) and of the peptide from the resin is carried out at zero degrees centigrade or below, preferably $-20°$ C. for thirty minutes followed by thirty minutes at $0°$ C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., *Methods in Enzymology*, 68:109 (1979). See also, J. Sambrook, et al., supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest. P In general, prokaryotes are used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
|---|---|
| DH5α | F-($\phi$80dlacZΔM15), Δ(lacZYA-argF)U169 supE44, λ-, hsdR17($r_K^-$, $m_K^+$), recA1, endA1, gyrA96, thi-1, relA1 |
| HB101 | supE44, hsdS20($r_B^-$ $m_B^-$), recA13, ara-14, proA2 lacY1, galK2, rpsL20, xyl-5, mtl-1, mcrB, mrr |
| JM109 | recA1, e14-(mcrA), supE44, endA1, hsdR17($r_K^-$, $m_K^+$), gyrA96, relA1, thi-1, Δ(lac-proAB), F'[traD36, proAB+ lacI9,lacZΔM15] |
| RR1 | supE44, hsdS20($r_B^-$ $m_B^-$), ara-14 proA2, |

-continued

| Strain | Genotype |
|---|---|
| χ1776 | lacY1, galK2, rpsL20, xyl-5, mtl-5 F⁻, ton, A53, dapD8, minA1, supE42 (glnV42), Δ(gal-uvrB)40, minB2, rfb-2, gyrA25, thyA142, oms-2, metC65, oms-1, Δ(bioH-asd)29, cycB2, cycA1, hsdR2, λ⁻ |
| 294 | endA, thi⁻, hsr⁻, hsm$_k$⁺ (U.S. Pat. No. 4,366,246) |

These strains are all commercially available from suppliers such as: Bethesda Research Laboratories, Gaithersburg, Md. 20877 and Stratagene Cloning Systems, La Jolla, Calif. 92037; or are available from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra.

In addition to the strains of *E. coli* discussed supra, bacilli such as *Bacillus subtilis*, other enterobacteriaceae such as *Salmonella typhimurium* or *Serratia marcescans*, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., *Nature* (London), 275:615 (1978); and Goeddel et al., *Nature* (London), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in *Protein Purification: From Molecular Mechanisms to Large Scale Processes*, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the human serotonin receptor-encoding nucleic acids of the present invention. Exemplary host cells suitable for use in the present invention are listed in Table I.

TABLE I

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7.1 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| HS-Sultan | Human Plasma Cell Plasmocytoma | ATCC CCL 1484 |
| BHK-21 | Baby Hamster Kidney | ATCC CCL 10 |

An especially preferred cell line employed in this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., J. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences* (USA), 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

The most preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. Nos. 5,242,688, issued Sep. 7, 1993, and 4,992,373, issued Feb. 12, 1991, as well as co-pending U.S. patent application Ser. No. 07/368,700, now abandoned, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

Figure 2:
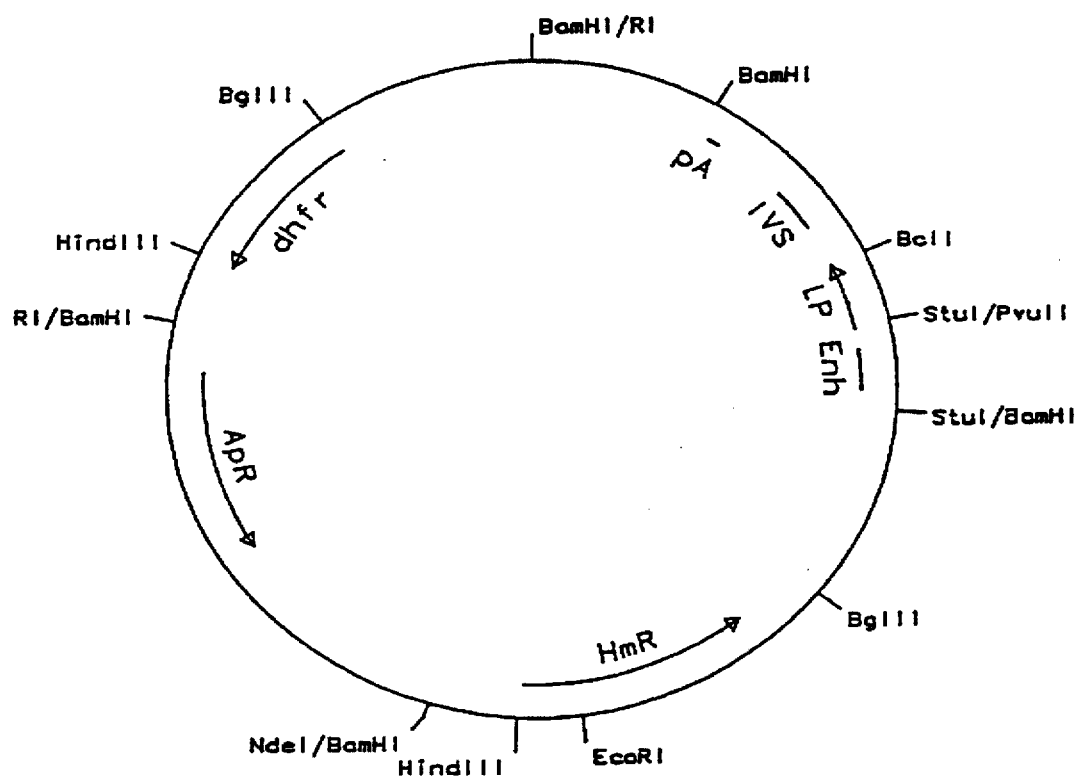
FIG. 2 is a restriction and function map of the plasmid phd. The term "dhfr" refers to the enzyme dihydrofolate reductase, "ApR" refers to the gene encoding ampicillin resistance, and "HmR" refers to the gene encoding hygromycin resistance. The term "Enh" refers to the BK virus enhancer, "LP" to the adenovirus later promoter, "IVS" refers to an intervening sequence (intron), and "pA" refers to a polyadenylation site.

The plasmid phd contains a unique BclI site which may be utilized for the insertion of the gene encoding the protein of interest. The skilled artisan understands that linkers or adapters may be employed in cloning the gene of interest into this BclI site. A depiction of the plasmid phd is provided as FIG. 2 of this document. The phd series of plasmids functions most efficiently when introduced into a host cell which produces the E1A gene product, cell lines such as AV12-664, 293 cells, and others, described supra.

Transformation of the mammalian cells can be performed by any of the known processes including, but not limited to, the protoplast fusion method, the calcium phosphate co-precipitation method, electroporation and the like. See, e.g., J. Sambrook, et al., supra, at 3:16.30–3:16.66.

Other routes of production are well known to skilled artisans. In addition to the plasmid discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See, e.g., L. Stinchcomb, et al., *Nature*, 282:39 (1979); J. Kingsman et al., *Gene*, 7:141 (1979); S. Tschemper et al., *Gene*, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjuction with the CYC1 promoter on plasmid YEpsec—hI1beta ATCC 67024), also are advantageously used with yeast promoters.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the protein of SEQ ID NO:2 are shown in Table II.

TABLE II

| Original Residue | Exemplary Substitutions |
|---|---|
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Met | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human serotonin 5-HT$_{2B}$ receptor molecule may be produced using synthetic methodology. This synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the receptor gene are generated using conventional DNA synthesizing apparatus such as the Applied Biosystems Model 380A or 3805 DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. [See, e.g., M. J. Gait, ed., *Oligonucleotide Synthesis, A Practical Approach*, (1984).]

The synthetic human serotonin 5-HT$_{2B}$ receptor gene may be designed to possess restriction endonuclease cleavage sites at either end of the transcript to facilitate isolation from and integration into expression and amplification plasmids. The choice of restriction sites are chosen so as to properly orient the coding sequence of the receptor with control sequences to achieve proper in-frame reading and expression of the 5-HT$_{2B}$ receptor molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid of SEQ ID NO:1, this invention also provides ribonucleic acids (RNA) which comprise the RNA sequence

| | |
|---|---|
| AUGGCUCUCUCUUACAGAGUGUCUGAACUUCAAAGCACAAUUCCUGAGCA | 50 |
| CAUUUUGCAGAGCACCUUUGUUCACGUUAUCUCUUCUAACUGGUCUGGAU | 100 |
| UACAGACAGAAUCAAUACCAGAGGAAAUGAAACAGAUUGUUGAGGAACAG | 150 |
| GGAAAUAAACUGCACUGGGCAGCUCUUCUGAUACUCAUGGUGAUAAUACC | 200 |
| CACAAUUGGUGGAAAUACCCUUGUUAUUCUGGCUGUUUCACUGGAGAAGA | 250 |
| AGCUGCAGUAUGCUACUAAUUACUUUCUAAUGUCCUUGGCGGUGGCUGAU | 300 |
| UUGCUGGUUGGAUUGUUUGUGAUGCCAAUUGCCCUCUUGACAAUAAUGUU | 350 |
| UGAGGCUAUGUGGCCCUCCCACUUGUUCUAUGUCCUGCCUGGUUAUUUC | 400 |
| UUGACGUUCUCUUUUCAACCGCAUCCAUCAUGCAUCUCUGUGCCAUUUCA | 450 |
| GUGGAUCGUUACAUAGCCAUCAAAAAGCCAAUCCAGGCCAAUCAAUAUAA | 500 |
| CUCACGGGCUACAGCAUUCAUCAAGAUUACAGUGGUGUGGUUAAUUUCAA | 550 |
| UAGGCAUUGCCAUUCCAGUCCCUAUUAAAGGGAUAGAGACUGAUGUGGAC | 600 |
| AACCCAAACAAUAUCACUUGUGUGCUGACAAAGGAACGUUUUGGCGAUUU | 650 |
| CAUGCUCUUUGGCUCACUGGCUGCUUCUUCACACCUCUUGCAAUUAUGA | 700 |
| UUGUCACCUACUUUCUCACUAUCCAUGCUUUACAGAAGAAGGCUUACUUA | 750 |
| GUCAAAAACAAGCCACCUCAACGCCUAACAUGGUUGACUGUGUCUACAGU | 800 |
| UUUCCAAAGGGAUGAAACACCUUGCUCGUCACCGGAAAAGGUGGCAAUGC | 850 |
| UGGAUGGUUCUCGAAAGGACAAGGCUCUGCCCAACUCAGGUGAUGAAACA | 900 |
| CUUAUGCGAAGAACAUCCACAAUUGGGAAAAAGUCAGUGCAGACCAUUUC | 950 |
| CAACGAACAGAGAGCCUCAAAGGUCCUAGGGAUUGUGUUUUUCCUCUUUU | 1000 |
| UGCUUAUGUGGUGUCCCUUCUUUAUUACAAAUAUAACUUUAGUUUUAUGU | 1050 |
| GAUUCCUGUAACCAAACUACUCUCCAAAUGCUCCUGGAGAUAUUUGUGUG | 1100 |
| GAUAGGCUAUGUUUCCUCAGGAGUGAAUCCUUUGGUCUACACCCUCUUCA | 1150 |
| AUAAGACAUUUCGGGAUGCAUUUGGCCGAUAUAUCACCUGCAAUUACCGG | 1200 |

```
GCCACAAAGUCAGUAAAAACUCUCAGAAAACGCUCCAGUAAGAUCUACUU    1250
CCGGAAUCCAAUGGCAGAGAACUCUAAGUUUUUCAAGAAACAUGGAAUUC    1300
GAAAUGGGAUUAACCCUGCCAUGUACCAGAGUCCAAUGAGGCUCCGAAGU    1350
UCAACCAUUCAGUCUUCAUCAAUCAUUCUACUAGAUACGCUUCUCCUCAC    1400
UGAAAAUGAAGGUGACAAAACUGAAGAGCAAGUUAGUUAUGUAUAG        1446
``` hereinafter referred to as SEQ ID NO:3 or a fragment thereof. The ribonucleic acids of the present invention may be prepared using the polynucleotide synthetic methods discussed supra or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to either SEQ ID NO:1 or SEQ ID NO:3.

The present invention also provides probes and primers useful for molecular biology techniques. A compound which encodes for SEQ ID NO:1, SEQ ID NO:3, a complementary sequence of either SEQ ID NO:1 or SEQ ID NO:3, or a fragment thereof, and which is at least 18 base pairs in length, and which will selectively hybridize to human genomic DNA or messenger RNA encoding a human serotonin receptor, is provided. Preferably, the 18 or more base pair compound is DNA.

The term "selectively hybridize" as used herein may refer to either of two situations. In the first such embodiment of this invention, the nucleic acid compounds described supra hybridize to a human serotonin receptor under more stringent hybridization conditions than these same nucleic acid compounds would hybridize to an analogous serotonin receptor of another species, e.g. murine or primate. In the second such embodiment of this invention, these probes hybridize to the 5-HT$_{2B}$ receptor under more stringent hybridization conditions than other related compounds, including nucleic acid sequences encoding other serotonin receptors.

These probes and primers can be prepared enzymatically as described supra. In a most preferred embodiment these probes and primers are synthesized using chemical means as described supra. Probes and primers of defined structure may also be purchased commercially.

This invention also encompasses recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprises the isolated DNA sequence SEQ ID NO:1. Plasmid pHu5HT$_{2B}$, which has been deposited with the NRRL and is available under accession number NRRL B-21160, is an especially preferred DNA vector of the present invention.

The plasmid pHu5HT$_{2B}$ was prepared by hybridizing to a human placental genomic library (commercially available from Stratagene) a radiolabeled probe derived from the sequence of the rat stomach fundus as published in M. Foguet, et al., EMBO Journal, 11:3481–3487 (1992) and described in co-pending U.S. patent application Ser. No. 07/864,005, filed Apr. 9, 1992, now abandoned. This probe, derived from putative transmembrane regions (nucleotides 751–1077 as listed in the aforementioned co-pending U.S. application) was labeled with [α-$^{32}$P]-deoxycytidinetriphosphate using primers (one corresponding to the nucleotides 751–776 and the other to the complement of nucleotides 1048–1077 as numbered in the aforementioned co-pending U.S. application) and the polymerase chain reaction. This probe was hybridized to the placental genomic library under low stringency conditions (30° C., 30% formamide) to isolate a number of clones having homologous sequences. None of these clones, or any combination thereof, contained a full length gene encoding the protein of interest, but these clones did produce a total of 778 base pairs of non-overlapping sequence, allowing the development of longer, more specific probes.

After performing tissue distribution studies to determine which tissues were most likely to express full length messenger RNA, a cDNA library of human uterine tissue was prepared employing the bacteriophage lambda gt-22. J. H. Han and W. J. Rutter, Nucleic Acids Research, 15:6304 (1987); commercially available from Bethesda Research Laboratories. This library was then probed with a 326 base pair fragment under relatively stringent hybridization conditions, permitting the isolation of several clones, the combination of which encoded the entire protein of interest. Large scale phage cultures for DNA isolation were prepared from those clones harboring the largest cDNA inserts, using standard methods. J. Sambrook, et al., supra. The purified cDNA inserts were subcloned into the plasmid vector pSPORT-1 (Bethesda Research Laboratories) for sequencing. The plasmid pSPORT-1 is an E. coli cloning vector containing the origin of replication from the pUC series of vectors, the β-lactamase gene conferring ampicillin resistance, a multiple cloning site, the bacteriophage f1 intergenic region for synthesis of single-stranded DNA, the α-peptide of the lacz gene, and SP6 and T7 promoters flanking the multiple cloning site.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

Plasmid pHu5HT$_{2B}$ may be isolated from the deposited *E. coli* containing the pHu5HT$_{2B}$ plasmid (*E. Coli*/pHu5HT$_{2B}$) using standard procedures such as cesium chloride DNA isolation. Cleaving of this plasmid with the restriction enzymes SalI and NotI results in the release of a 2338 basepairs fragment of the sequence ety of organisms, including, for example, *E. coli*, Sf9 (as host for baculovirus), Spodoptera and Saccharomyces. The current literature contains techniques for constructing AV12 expression vectors and for transforming AV12 host cells. U.S. Pat. No. 4,992,373, herein incorporated by reference, is one of many references describing these techniques.

One of the most widely employed techniques for altering a nucleic acid sequence is by way of oligonucleotide-directed site-specific mutagenesis. B. Comack, "Current Protocols in Molecular Biology", 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In the most preferred embodiment of this technique, the template is a single-stranded template. As noted Supra, the plasmid pSPORT-1, the parent plasmid from which pHu5HT2B was constructed, contains the f1 intergenic region. This region allows the generation of single-stranded templates when a helper phage is added to the culture harboring the "phagemid".

| | | | | | | | |
|---|---|---|---|---|---|---|---|
| CCCACGCGTC | CGCAATGGGA | GGAGGATTTC | AGTCACAGCA | GCAAGCAAGT | CTAGTGAACA | | 60 |
| GATAAGATGA | CATGCTCAGC | AAAATAACAA | CGAAACCAGA | GGGGGAACTC | TCTGGCATGC | | 120 |
| AAGTTCAAAC | ACGACTCTAC | AACTACGGCA | GAAAAAGAGA | GAGAGAGAAA | CTAAAAATAT | | 180 |
| ATATATATCC | TATTTTTTTC | ACAGCTATCA | GTTTCTTTCA | CTGAGCTTTC | CTAAATTTAA | | 240 |
| GCCTCTAGAA | AATAATAAAT | ACTTGGATAT | CTTACCTACA | AACATGGACA | GATGTGTGTA | | 300 |
| TGCGCTCATT | TTAGAGAACT | TGAATTTTTT | TTTTTAAAGG | AAGGTGTCAA | CTTTGGCTTT | | 360 |
| TGAGTGTTTG | GCATGGTTAC | AATGCCTTAA | AAAAACAGAT | GAGCAGCTTA | GCTACTAACC | | 420 |
| ATGCTGACCA | CTGTTCGGAA | CGGGATTGAA | TCACAGAAAA | ACAGCAAATG | GCTCTCTCTT | | 480 |
| ACAGAGTGTC | TGAACTTCAA | AGCACAATTC | CTGAGCACAT | TTTGCAGAGC | ACCTTTGTTC | | 540 |
| ACGTTATCTC | TTCTAACTGG | TCTGGATTAC | AGACAGAATC | AATACCAGAG | GAAATGAAAC | | 600 |
| AGATTGTTGA | GGAACAGGGA | AATAAACTGC | ACTGGGCAGC | TCTTCTGATA | CTCATGGTGA | | 660 |
| TAATACCCAC | AATTGGTGGA | AATACCCTTG | TTATTCTGGC | TGTTTCACTG | GAGAAGAAGC | | 720 |
| TGCAGTATGC | TACTAATTAC | TTTCTAATGT | CCTTGGCGGT | GGCTGATTTG | CTGGTTGGAT | | 780 |
| TGTTTGTGAT | GCCAATTGCC | CTCTTGACAA | TAATGTTTGA | GGCTATGTGG | CCCCTCCCAC | | 840 |
| TTGTTCTATG | TCCTGCCTGG | TTATTTCTTG | ACGTTCTCTT | TTCAACCGCA | TCCATCATGC | | 900 |
| ATCTCTGTGC | CATTTCAGTG | GATCGTTACA | TAGCCATCCA | AAAGCCAATC | CAGGCCAATC | | 960 |
| AATATAACTC | ACGGGCTACA | GCATTCATCA | AGATTACAGT | GGTGTGGTTA | ATTTCAATAG | | 1020 |
| GCATTGCCAT | TCCAGTCCCT | ATTAAAGGGA | TAGAGACTGA | TGTGGACAAC | CCAAACAATA | | 1080 |
| TCACTTGTGT | GCTGACAAAG | GAACGTTTTG | GCGATTTCAT | GCTCTTTGGC | TCACTGGCTG | | 1140 |
| CCTTCTTCAC | ACCTCTTGCA | ATTATGATTG | TCACCTACTT | TCTCACTATC | CATGCTTTAC | | 1200 |
| AGAAGAAGGC | TTACTTAGTC | AAAAACAAGC | CACCTCAACG | CCTAACATGG | TTGACTGTGT | | 1260 |
| CTACAGTTTT | CCAAAGGGAT | GAAACACCTT | GCTCGTCACC | GGAAAAGGTG | GCAATGCTGG | | 1320 |
| ATGGTTCTCG | AAAGGACAAG | GCTCTGCCCA | ACTCAGGTGA | TGAAACACTT | ATGCGAAGAA | | 1380 |
| CATCCACAAT | TGGGAAAAGA | TCAGTGCAGA | CCATTTCCAA | CGAACAGAGA | GCCTCAAAGG | | 1440 |
| TCCTAGGGAT | TGTGTTTTTC | CTCTTTTTGC | TTATGTGGTG | TCCCTTCTTT | ATTACAAATA | | 1500 |
| TAACTTTAGT | TTTATGTGAT | TCCTGTAACC | AAACTACTCT | CCAAATGCTC | CTGGAGATAT | | 1560 |
| TTGTGTGGAT | AGGCTATGTT | TCCTCAGGAG | TGAATCCTTT | GGTCTACACC | CTCTTCAATA | | 1620 |
| AGACATTTCG | GGATGCATTT | GGCCGATATA | TCACCTGCAA | TTACCGGGCC | ACAAAGTCAG | | 1680 |
| TAAAAACTCT | CAGAAAACGC | TCCAGTAAGA | TCTACTTCCG | GAATCCAATG | GCAGAGAACT | | 1740 |
| CTAAGTTTTT | CAAGAAACAT | GGAATTCGAA | ATGGGATTAA | CCCTGCCATG | TACCAGAGTC | | 1800 |
| CAATGAGGCT | CCGAAGTTCA | ACCATTCAGT | CTTCATCAAT | CATTCTACTA | GATACGCTTC | | 1860 |
| TCCTCACTGA | AAATGAAGGT | GACAAAACTG | AAGAGCAAGT | TAGTTATGTA | TAGCTGAGAG | | 1920 |
| CCAGTCAGTA | TGTATCGCAG | CACTGGCAGT | TGTCGTCAAA | CATAATGATG | AGTAAGATGA | | 1980 |
| TGAATGAGAT | GTAAATGTGC | CAAGAATATA | TTATATAAAG | AATTTTATGT | CATATATCAA | | 2040 |
| ATCATCTCTT | TAACCTAAGA | TGTAAGTATT | AAGAATATCT | AATTTTCCTA | ATTTGGACAA | | 2100 |
| GATTATTCCA | TGAGGAAAAT | AATTTTATAT | AGCTACAAAT | GAAAACAATC | CAGCACTCTG | | 2160 |
| GTTAAATTTT | AAGGTATTCG | AATGAAATAA | AGTCAAATCA | ATAAATTTCA | GGCTTTAAAA | | 2220 |
| AGAAAAAAAA | AAAAAAAA | | | | | | 2238 | hereinafter referred to as SEQ ID NO:4, in combination with the 5' overhanging ends generated by the cleavage with these two enzymes. In this fragment the SalI site of the parent pSPORT-1 vector is located immediately adjacent to the 5' end of the sequence as depicted, with the NotI site of the parent pSPORT-1 vector being situated immediately adjacent to the 3' end of the sequence as it is depicted above. The relative locations of these restriction sites and the direction of translation of the proteins of the instant invention are depicted in FIG. 1.

Plasmid pHu5HT$_{2B}$ is readily modified to construct expression vectors that produce 5-HT$_{2B}$ receptors in a vari- After the annealing of the oligonucleotide to the template, a DNA-dependent DNA polymerase is then used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for *E. coli* can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and *E. coli* cells which have been transfected and/or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is AV12. The preferred vector for expression is one which comprises SEQ ID NO:1. Another preferred host cell for this method is *E. coli*. An especially preferred expression vector in *E. coli* is one which comprises SEQ ID NO:1. Transformed host cells may be cultured under conditions well known to skilled artisans such that SEQ ID NO:2 is expressed, thereby producing 5-$HT_{2B}$ in the recombinant host cell.

The ability of serotonin to bind to the 5-$HT_{2B}$ receptor is essential in the development of a multitude of indications. In developing agents which act as antagonists or agonists of the 5-$HT_{2B}$ receptor, it would be desirable, therefore, to determine those agents which bind the 5-$HT_{2B}$ receptor. Generally, such an assay includes a method for determining whether a substance is a functional ligand of the 5-$HT_{2B}$ receptor, said method comprising contacting a functional compound of the 5-$HT_{2B}$ receptor with said substance, monitoring binding activity by physically detectable means, and identifying those substances which effect a chosen response. Preferably, the physically detectable means is competition with labeled serotonin or binding of ligand in an oocyte transient expression system The instant invention provides such a screening system useful for discovering agents which compete with serotonin for binding to the 5-$HT_{2B}$ receptor, said screening system comprising the steps of:

a) isolating a human 5-$HT_{2B}$ receptor;

b) exposing said human 5-$HT_{2B}$ receptor to a potential inhibitor or surrogate of the serotonin/5-$HT_{2B}$ receptor complex;

c) introducing serotonin;

d) removing non-specifically bound molecules; and e) quantifying the concentration of bound potential inhibitor and/or serotonin.

This allows one to rapidly screen for inhibitors or surrogates of the formation of the serotonin/5-$HT_{2B}$ receptor complex. Utilization of the screening system described above provides a sensitive and rapid means to determine compounds which interfere with the formation of the serotonin/5-$HT_{2B}$ receptor complex. This screening system may also be adapted to automated procedures such as a Pandex® (Baxter-Dade Diagnostics) system allowing for efficient high-volume screening of potential therapeutic agents.

In such a screening protocol a 5-$HT_{2B}$ receptor is prepared as elsewhere described herein, preferably using recombinant DNA technology. A sample of a test compound is then introduced to the reaction vessel containing the 5-$HT_{2B}$ receptor followed by the addition of serotonin. In the alternative the serotonin may be added simultaneously with the test compound. Unbound molecules are washed free and the eluent inspected for the presence of serotonin or the test compound.

For example, in a preferred method of the invention, radioactively or fluorescently labeled serotonin may be used. The eluent is then scored for fluorescence or radioactivity. The absence or diminution of fluorescence or radioactivity indicates the formation of the serotonin/5-$HT_{2B}$ receptor complex. This indicates that the test compound has not effectively competed with serotonin in the formation of the serotonin/5-$HT_{2B}$ receptor complex. The presence of fluorescence or radioactivity indicates that the test compound has competed with serotonin in the formation of the serotonin/5-$HT_{2B}$ receptor complex. Similarly, a radioactively or fluorescently labeled test compound may be used in which case the same steps as outlined above would be used except that the interpretation of results would be the converse of using radioactively or fluorescently labelled serotonin.

As would be understood by the skilled artisan these assays may also be performed such that the practitioner measures the radioactivity or fluorescence remaining with the protein, not in the eluent. A preferred such assay employs radiolabeled serotonin. After the competition reaction has been performed the reaction mixture is then passed through a filter, the filter retaining the receptor and whatever is complexed with the receptor. The radioactivity on each filter is then measured in a scintillation counter. In such an assay higher amounts of radiolabel present indicate lower affinity for the receptor by the test compound.

The 5-$HT_{2B}$ receptor may be free in solution or bound to a solid support. Whether the 5-$HT_{2B}$ receptor is bound to a support or is free in solution, it is generally important that the conformation of the protein be conserved. In a preferred practice of the invention, therefore, the 5-$HT_{2B}$ receptor is suspended in a hydrophobic environment employing natural or synthetic detergents, membrane suspensions, and the like. Preferred detergent complexes include the zwitterionic detergent 3-[(3-cholamidopropyl)-dimethylammonio]-1-propane sulfonate ("CHAPS") as well as sodium deoxycholate.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom indicate high affinity or low affinity to 5-$HT_{2B}$ receptor, because skilled artisans will recognize that any information regarding binding or selectivity of a particular compound is beneficial in the pharmaceutical development of drugs.

In one such competition assay, a battery of known serotonin receptor antagonists, agonists, and partial agonists were evaluated for their relative abilities to inhibit the binding of [$^3$H]5-hydroxytryptamine to the human 5-$HT_{2B}$ receptor of the present invention.

In this assay suspension cells stably expressing the cloned human 5-$HT_{2B}$ receptor were harvested by centrifugation at 2200×g for 15 minutes at 4° C. Membranes for the binding assays were prepared by vortexing the cell pellet in 50 mM Tris.HCl, pH 7.4 (0.5×10$^9$ cells/30 ml). The tissue suspension was then centrifuged at 39,800×g for 10 minutes at 4°

C. This procedure was repeated for a total of three washes, with a 10 minute incubation at 37° C. between the second and third washes. The final pellet was homogenized in 67 mM Tris.HCl, pH 7.4, at $12.5 \times 10^6$ cells/ml using a Tissumizer® (Tekmar, Cincinati, Ohio) at setting 65 for 15 seconds.

Binding assays were performed in triplicate in 0.8 ml total volume. Volumes of 200 µl of membrane suspension (0.07–0.10 mg of protein) and 200 µl of drug dilution in water were added to 400 µl of 67 mM of Tris.HCl, pH 7.4, containing [$^3$H]serotonin (35 nM final concentration, 23.7 Ci/mole), calcium chloride (3 mM), pargyline (10 µM, and L-ascorbic acid (5.7 nM). The reaction mixtures were incubated at 37° C. for 15 minutes and then rapidly filtered, using a Brandel™ cell harvester (Model MB-48R; Brandel, Gaithersburg, Md.) over Whatman GF/B filters that had been presoaked in 0.5% polyethyleneimine and precooled with ice-cold 50 mM Tris-HCl, pH 7.4. The filters were then washed rapidly times with ice-cold (4×1 ml each).

The amount of [$^3$H]serotonin trapped on the filters was determined by liquid scintillation counting. For the competition experiments, six concentrations of displacing drugs were used, ranging from $10^{-5}$ to $10^{-10}$M. The IC$_{50}$ values were determined by nonlinear regression analysis (Systat™; Systat Inc., Evanston, Ill.) which may be converted to K$_i$ values using the Cheng-Prusoff equation. Y. Cheng and W. H. Prusoff, *Biochemical Pharmacology*, 22:3099–3108 (1973).

In this particular competition assay the following compounds were used.

(a) Ketanserin—a compound of the formula

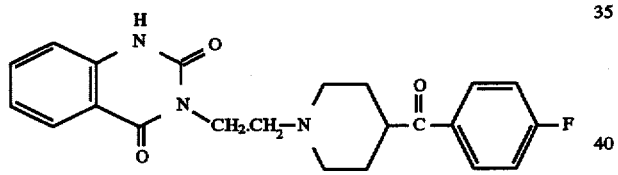

having the chemical name 3-[2-[4-(4-fluorobenzoyl)-1-piperidinyl]ethyl]-2,4[1H, 3H]-quinazolinedione. This compound—which can be prepared as described in U.S. Pat. No. 4,335,127, herein incorporated by reference—is a specific serotonin S$_2$-receptor antagonist with hypotensive properties.

(b) Spiperone—a compound of the formula

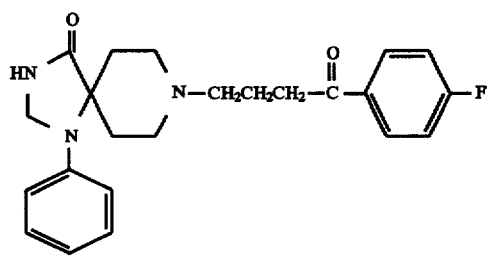

having the chemical name 8-[4-(4-fluorophenyl)4-oxobutyl]-1-phenyl-1,3,8-triazaspiro[4,5]decan-4-one. This compound can be prepared as described in U.S. Pat. Nos. 3,155,669, 3,155,670, and 3,161,644, all of which are herein incorporated by reference.

(c) Rauwolscine—a compound of the formula

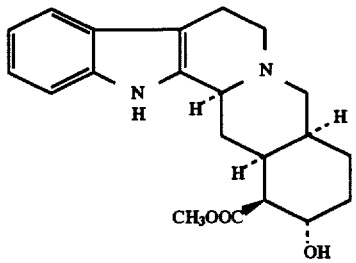

having the chemical name 17α-hydroxy-20α-yohimban-16β-carboxylic acid methyl ester. This compound, also known as α-yohimbine, can be prepared as described in Töke, et al., *Journal of Organic Chemistry*, 38:2496 (1973) or can be purchased commercially from many sources.

(d) Yohimbine—a compound also known as alloyohimbine having the formula

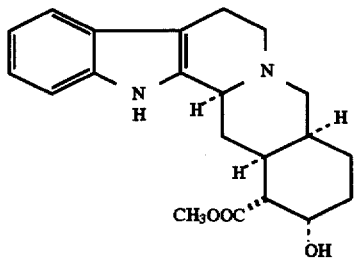

with the chemical name 17-hydroxyyohimban-16-carboxylic acid methyl ester. This compound, which is available from commercial sources, can also be synthesized as described in Töke, et al., supra.

(e) Serotonin—a compound having the formula

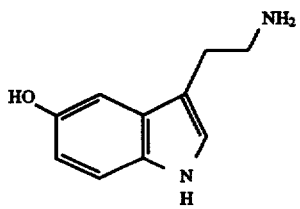

which is also known as 5-hydroxytryptamine (5-HT) and 3-(2-aminoethyl)-1H-indol-5-ol is available commercially or can be synthesized as described in U.S. Pat. No. 2,715,129, which is herein incorporated by reference.

(f) α-Methyl-5-hydroxytryptamine—a compound of the formula

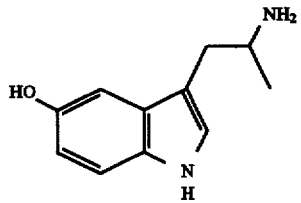

having the chemical name 3-(2-aminopropyl)-1H-indol-5-ol, which can be purchased from commercial sources.

(g) 1-(1-Naphthyl)piperazine—a compound of the formula

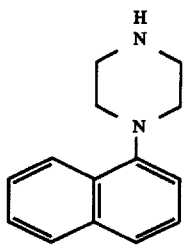

which is described in U.S. Pat. No. 4,520,024, issued May 28, 1985, which is herein incorporated by reference.

The following table, Table III, gives the results of one such assay. The $IC_{50}$ is the concentration of the compound, in nanomolar amounts, which displaces or inhibits the binding of 50% of the labeled 5-hydroxytryptamine.

TABLE III

| Compound | $IC_{50}$ (nM) |
| --- | --- |
| ketanserin | 346 |
| spiperone | 691 |
| yohimbine | 20.2 |
| serotonin | 12.5 |
| rauwolscine | 37.5 |
| α-methyl-5-hydroxytryptamine | 11.8 |
| 1-(1-naphthyl)piperazine | 2.41 |

The previously described screening system identifies compounds which competitively bind to the 5-$HT_{2B}$ receptor. Determination of the ability of such compounds to stimulate or inhibit the action of the 5-$HT_{2B}$ receptor is essential to further development of such compounds for therapeutic applications. The need for a bioactivity assay system which determines the response of the 5-$HT_{2B}$ receptor to a compound is clear. The instant invention provides such a bioactivity assay, said assay comprising the steps of:
a) transfecting a mammalian host cell with an expression vector comprising DNA encoding a 5-$HT_{2B}$ receptor;
b) culturing said host cell under conditions such that the DNA encoding the 5-$HT_{2B}$ receptor is expressed,
c) exposing said host cell so transfected to a test compound, and
d) measuring the change in a physiological condition known to be influenced by the binding of serotonin to the 5-$HT_{2B}$ receptor relative to a control in which the transfected host cell is exposed to serotonin.

An oocyte transient expression system can be constructed according to the procedure described in S. Lübbert, et al., *Proceedings of the National Academy of Sciences* (USA), 84:4332 (1987).

In an especially preferred embodiment of this invention an assay which correlates serotonergic activity with the hydrolysis of phosphatidylinositol was performed. The hydrolysis of phosphatidylinositol is known to positively correlate with addition of serotonin. This biochemical assay was performed essentially as described by M. Berridge, *Biochemistry Journal*, 212:849 (1983).

In essence, the wells of a 12 well plate were seeded with enough cells in 1.0 milliliter of media containing 4.0 µCi of myo-[$^3$H]-inositol such that confluency was obtained in 48 hours (for AV12 cells this is 5×10$^5$ cells). After 48 hours in tissue culture incubator the media was aspirated and the cells were washed twice with serum-free media containing 10 mM myoinositol and 10 mM lithium chloride. After the final wash 1.0 ml of the supplemented serum-free media used supra was added to each well.

Dilutions of the appropriate compounds were then added to the appropriate wells and the plate was floated in a 37° C. water bath for the appropriate time (usually 1 hour). The reaction was terminated by aspirating the media and adding 0.5 ml of ice-cold acetone:methanol (1:1, v:v). The plate was left on a rocking platform for 20 minutes at 4° C.

The extract from each well was then harvested into a microcentrifuge tube. Each well was rinsed well with 0.5 ml water which was combined with the extracts.

The samples were centrifuged in a microfuge for about 10 minutes to pellet cellular residue. The supernatant from each well was then loaded onto a separate Sep-Pak Waters Accell Plus QMA Cartridge™ which had been previously treated. In this previous treatment the formate form of the resin was prepared by first adding 10 mls of 1M ammonium formate, 0.1M formic acid to each cartridge and drawing this through the cartridge by vacuum. Each cartridge was then washed twice with 10 mls water.

Water (0.5 ml) was then added to each of the samples. The diluted samples were drawn through the cartridges by vacuum.

After each sample had gone through the cartridge, 10 mls of 5.0 mM sodium tetraborate was drawn through each cartridge. The samples were then placed in 20 ml scintillation vials, 4.0 mls of 0.1M ammonium formate, 0.01M formic acid, 5 mM sodium tetraborate was added to the cartridges and drawn into vials with vacuum. Scintillation fluid was then added to each vial and the vials were counted.

A graphing of the amount of radiolabeled material in the sample against the amount of the test compound introduced in that particular experiment allows one to assess the serotonergic activity of the particular test compound. Comparison of the concentration of test compound which gives fifty percent of the maximum biochemical activity (termed "$EC_{50}$" meaning the concentration of compound providing 50% of the effective concentration) with a similar $EC_{50}$ calculated for serotonin aids the investigator in evaluating whether the test compound is an effective agonist or partial agonist at this receptor.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', Fab$_2$',and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See, e.g., C. Milstein, *Handbook of Experimental Immunology*, (Blackwell Scientific Pub., 1986); J. Goding, *Monoclonal Antibodies: Principles and Practice*, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See, e.g. R. E. Bird, et al., *Science* 242:423–426 (1988); PCT Publication No. WO 88/01649, which was published 10 Mar. 1988. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of 5-HT$_{2B}$ receptors.

In addition to being functional as direct therapeutic and diagnostic aids, the availability of a family of antibodies which are specific for the 5-HT$_{2B}$ receptor enables the development of numerous assay systems for detecting agents which bind to this receptor. One such assay system comprises radiolabeling 5-HT$_{2B}$ receptor-specific antibodies with a radionuclide such as $^{125}$I and measuring displacement of the radiolabeled 5-HT$_{2B}$ receptor-specific antibody from solid phase 5-HT$_{2B}$ receptor in the presence of a potential antagonist.

Numerous other assay systems are also readily adaptable to detect agents which bind 5-HT$_{2B}$ receptor. Examples of these aforementioned assay systems are discussed in *Methods in Enzymology*, (J. Langone. and H. Vunakis, eds. 1981), Vol. 73, Part B, the contents of which are herein incorporated by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for the 5-HT$_{2B}$ receptor, this invention also provides antibodies which are specific for the hypervariable regions of the anti-5-HT$_{2B}$ receptor antibodies. Some such anti-idiotypic antibodies would resemble the original epitope, the 5-HT$_{2B}$ receptor, and, therefore, would be useful in evaluating the effectiveness of compounds which are potential antagonists, agonists, or partial agonists of the 5-HT$_{2B}$ receptor. See, e.g., Cleveland, et al., *Nature* (London), 305:56 (1983); Wasserman, et al., *Proceedings of the National Academy of Sciences* (USA), 79:4810 (1982).

In another embodiment, this invention encompasses pharmaceutical formulations for parenteral administration which contain, as the active ingredient, the anti-5-HT$_{2B}$ receptor antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

We claim:

1. An isolated nucleic acid compound encoding an amino acid compound which comprises the amino acid sequence:

Met Ala Leu Ser Tyr Arg Val Ser Glu Leu Gln Ser Thr Ile
1               5                       10
Pro Glu His Ile Leu Gln Ser Thr Phe Val His Val Ile Ser
15              20                      25
Ser Asn Trp Ser Gly Leu Gln Thr Glu Ser Ile Pro Glu Glu
        30              35                      40
Met Lys Gln Ile Val Glu Glu Gln Gly Asn Lys Leu His Trp
            45              50                      55
Ala Ala Leu Leu Ile Leu Met Val Ile Ile Pro Thr Ile Gly
                60              65                      70
Gly Asn Thr Leu Val Ile Leu Ala Val Ser Leu Glu Lys Lys
                    75              80
Leu Gln Tyr Ala Thr Asn Tyr Phe Leu Met Ser Leu Ala Val
85                      90                      95
Ala Asp Leu Leu Val Gly Leu Phe Val Met Pro Ile Ala Leu
100                     105                     110
Leu Thr Ile Met Phe Glu Ala Met Trp Pro Leu Pro Leu Val
            115                     120                 125
Leu Cys Pro Ala Trp Leu Phe Leu Asp Val Leu Phe Ser Thr
                130                     135                 140
Ala Ser Ile Met His Leu Cys Ala Ile Ser Val Asp Arg Tyr
                    145                     150
Ile Ala Ile Lys Lys Pro Ile Gln Ala Asn Gln Tyr Asn Ser
155                     160                     165
Arg Ala Thr Ala Phe Ile Lys Ile Thr Val Val Trp Leu Ile
170                     175                     180
Ser Ile Gly Ile Ala Ile Pro Val Pro Ile Lys Gly Ile Glu
            185                     190                     195
Thr Asp Val Asp Asn Pro Asn Asn Ile Thr Cys Val Leu Thr
            200                     205                     210
Lys Glu Arg Phe Gly Asp Phe Met Leu Phe Gly Ser Leu Ala
                215                     220
Ala Phe Phe Thr Pro Leu Ala Ile Met Ile Val Thr Tyr Phe
225                     230                     235
Leu Thr Ile His Ala Leu Gln Lys Lys Ala Tyr Leu Val Lys
240                     245                     250
Asn Lys Pro Pro Gln Arg Leu Thr Trp Leu Thr Val Ser Thr
    255                     260                     265
Val Phe Gln Arg Asp Glu Thr Pro Cys Ser Ser Pro Glu Lys
            270                     275                     280
Val Ala Met Leu Asp Gly Ser Arg Lys Asp Lys Ala Leu Pro
                285                     290
Asn Ser Gly Asp Glu Thr Leu Met Arg Arg Thr Ser Thr Ile
295                     300                     305
Gly Lys Lys Ser Val Gln Thr Ile Ser Asn Glu Gln Arg Ala
    310                     315                     320
Ser Lys Val Leu Gly Ile Val Phe Phe Leu Phe Leu Leu Met
    325                     330                     335
Trp Cys Pro Phe Phe Ile Thr Asn Ile Thr Leu Val Leu Cys
            340                     345                     350
Asp Ser Cys Asn Gln Thr Thr Leu Gln Met Leu Leu Glu Ile
                355                     360
Phe Val Trp Ile Gly Tyr Val Ser Ser Gly Val Asn Pro Leu
365                     370                     375
Val Tyr Thr Leu Phe Asn Lys Thr Phe Arg Asp Ala Phe Gly
    380                     385                     390
Arg Tyr Ile Thr Cys Asn Tyr Arg Ala Thr Lys Ser Val Lys
        395                     400                     405
Thr Leu Arg Lys Arg Ser Ser Lys Ile Tyr Phe Arg Asn Pro
        410                     415                     420
Met Ala Glu Asn Ser Lys Phe Phe Lys Lys His Gly Ile Arg
                425                     430
Asn Gly Ile Asn Pro Ala Met Tyr Gln Ser Pro Met Arg Leu
435                     440                     445
Arg Ser Ser Thr Ile Gln Ser Ser Ser Ile Ile Leu Leu Asp
    450                     455                     460
Thr Leu Leu Leu Thr Glu Asn Glu Gly Asp Lys Thr Glu Glu
        465                     470                     475
Gln Val Ser Tyr Val
            480 which is SEQ ID NO:2.

2. An isolated nucleic acid composition comprising a sequence encoding a human serotonin receptor identified herein as SEQ ID NO.2 wherein said sequence is selected from the group consisting of:

(a) SEQ ID NO 1;

(b) SEQ ID NO 3; and (c) nucleic acid compounds complementary to (a) or (b).

3. A composition as claimed in claim 2 wherein the isolated nucleic acid compound is deoxyribonucleic acid.

4. A composition as claimed in claim 3 which is (a) or a sequence complementary to (a).

5. A composition as claimed in claim 3 which is pHu5HT$_{2F}$.

6. An expression vector capable of producing a human serotonin receptor in a host cell which comprises a nucleic acid composition as claimed in claim 2 operably linked with regulatory elements necessary for expression of the nucleic acid compound in the host cell.

7. An expression vector as claimed in claim 6 wherein the host cell is *Escherichia coli*.

8. An expression vector as claimed in claim 6 wherein the host cell is a mammalian cell line.

9. An expression vector as claimed in claim 6 which comprises the BK virus enhancer.

10. An expression vector as claimed in claim 9 which further comprises an adenovirus late promoter.

11. A transfected host cell harboring an expression vector as claimed in claim 6.

12. A transfected host cell as claimed in claim 11 which is *Escherichia coli*.

13. A transfected host cell as claimed in claim 11 which is a mammalian cell line.

14. A transfected host cell as claimed in claim 13 which is AV-12.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1446 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1443

( x i ) SEQUENCE DESCRIPTION: SEQ ID NO:1:

```
ATG GCT CTC TCT TAC AGA GTG TCT GAA CTT CAA AGC ACA ATT CCT GAG      48
Met Ala Leu Ser Tyr Arg Val Ser Glu Leu Gln Ser Thr Ile Pro Glu
 1               5                  10                  15

CAC ATT TTG CAG AGC ACC TTT GTT CAC GTT ATC TCT TCT AAC TGG TCT      96
His Ile Leu Gln Ser Thr Phe Val His Val Ile Ser Ser Asn Trp Ser
            20                  25                  30

GGA TTA CAG ACA GAA TCA ATA CCA GAG GAA ATG AAA CAG ATT GTT GAG     144
Gly Leu Gln Thr Glu Ser Ile Pro Glu Glu Met Lys Gln Ile Val Glu
        35                  40                  45

GAA CAG GGA AAT AAA CTG CAC TGG GCA GCT CTT CTG ATA CTC ATG GTG     192
Glu Gln Gly Asn Lys Leu His Trp Ala Ala Leu Leu Ile Leu Met Val
 50                  55                  60

ATA ATA CCC ACA ATT GGT GGA AAT ACC CTT GTT ATT CTG GCT GTT TCA     240
Ile Ile Pro Thr Ile Gly Gly Asn Thr Leu Val Ile Leu Ala Val Ser
 65                  70                  75                  80

CTG GAG AAG AAG CTG CAG TAT GCT ACT AAT TAC TTT CTA ATG TCC TTG     288
Leu Glu Lys Lys Leu Gln Tyr Ala Thr Asn Tyr Phe Leu Met Ser Leu
                85                  90                  95

GCG GTG GCT GAT TTG CTG GTT GGA TTG TTT GTG ATG CCA ATT GCC CTC     336
Ala Val Ala Asp Leu Leu Val Gly Leu Phe Val Met Pro Ile Ala Leu
            100                 105                 110

TTG ACA ATA ATG TTT GAG GCT ATG TGG CCC CTC CCA CTT GTT CTA TGT     384
Leu Thr Ile Met Phe Glu Ala Met Trp Pro Leu Pro Leu Val Leu Cys
        115                 120                 125

CCT GCC TGG TTA TTT CTT GAC GTT CTC TTT TCA ACC GCA TCC ATC ATG     432
Pro Ala Trp Leu Phe Leu Asp Val Leu Phe Ser Thr Ala Ser Ile Met
    130                 135                 140

CAT CTC TGT GCC ATT TCA GTG GAT CGT TAC ATA GCC ATC AAA AAG CCA     480
His Leu Cys Ala Ile Ser Val Asp Arg Tyr Ile Ala Ile Lys Lys Pro
145                 150                 155                 160

ATC CAG GCC AAT CAA TAT AAC TCA CGG GCT ACA GCA TTC ATC AAG ATT     528
Ile Gln Ala Asn Gln Tyr Asn Ser Arg Ala Thr Ala Phe Ile Lys Ile
                165                 170                 175

ACA GTG GTG TGG TTA ATT TCA ATA GGC ATT GCC ATT CCA GTC CCT ATT     576
Thr Val Val Trp Leu Ile Ser Ile Gly Ile Ala Ile Pro Val Pro Ile
            180                 185                 190

AAA GGG ATA GAG ACT GAT GTG GAC AAC CCA AAC AAT ATC ACT TGT GTG     624
Lys Gly Ile Glu Thr Asp Val Asp Asn Pro Asn Asn Ile Thr Cys Val
        195                 200                 205

CTG ACA AAG GAA CGT TTT GGC GAT TTC ATG CTC TTT GGC TCA CTG GCT     672
Leu Thr Lys Glu Arg Phe Gly Asp Phe Met Leu Phe Gly Ser Leu Ala
    210                 215                 220
```

| | | | | | | | | | | | | | | | | |
|---|---|---|---|---|---|---|---|---|---|---|---|---|---|---|---|---|
| GCC | TTC | TTC | ACA | CCT | CTT | GCA | ATT | ATG | ATT | GTC | ACC | TAC | TTT | CTC | ACT | 720 |
| Ala | Phe | Phe | Thr | Pro | Leu | Ala | Ile | Met | Ile | Val | Thr | Tyr | Phe | Leu | Thr | |
| 225 | | | | 230 | | | | | 235 | | | | | | 240 | |
| ATC | CAT | GCT | TTA | CAG | AAG | AAG | GCT | TAC | TTA | GTC | AAA | AAC | AAG | CCA | CCT | 768 |
| Ile | His | Ala | Leu | Gln | Lys | Lys | Ala | Tyr | Leu | Val | Lys | Asn | Lys | Pro | Pro | |
| | | | | 245 | | | | | 250 | | | | | 255 | | |
| CAA | CGC | CTA | ACA | TGG | TTG | ACT | GTG | TCT | ACA | GTT | TTC | CAA | AGG | GAT | GAA | 816 |
| Gln | Arg | Leu | Thr | Trp | Leu | Thr | Val | Ser | Thr | Val | Phe | Gln | Arg | Asp | Glu | |
| | | | 260 | | | | | 265 | | | | | 270 | | | |
| ACA | CCT | TGC | TCG | TCA | CCG | GAA | AAG | GTG | GCA | ATG | CTG | GAT | GGT | TCT | CGA | 864 |
| Thr | Pro | Cys | Ser | Ser | Pro | Glu | Lys | Val | Ala | Met | Leu | Asp | Gly | Ser | Arg | |
| | | 275 | | | | | 280 | | | | | 285 | | | | |
| AAG | GAC | AAG | GCT | CTG | CCC | AAC | TCA | GGT | GAT | GAA | ACA | CTT | ATG | CGA | AGA | 912 |
| Lys | Asp | Lys | Ala | Leu | Pro | Asn | Ser | Gly | Asp | Glu | Thr | Leu | Met | Arg | Arg | |
| | 290 | | | | | 295 | | | | | 300 | | | | | |
| ACA | TCC | ACA | ATT | GGG | AAA | AAG | TCA | GTG | CAG | ACC | ATT | TCC | AAC | GAA | CAG | 960 |
| Thr | Ser | Thr | Ile | Gly | Lys | Lys | Ser | Val | Gln | Thr | Ile | Ser | Asn | Glu | Gln | |
| 305 | | | | | 310 | | | | | 315 | | | | | 320 | |
| AGA | GCC | TCA | AAG | GTC | CTA | GGG | ATT | GTG | TTT | TTC | CTC | TTT | TTG | CTT | ATG | 1008 |
| Arg | Ala | Ser | Lys | Val | Leu | Gly | Ile | Val | Phe | Phe | Leu | Phe | Leu | Leu | Met | |
| | | | | 325 | | | | | 330 | | | | | 335 | | |
| TGG | TGT | CCC | TTC | TTT | ATT | ACA | AAT | ATA | ACT | TTA | GTT | TTA | TGT | GAT | TCC | 1056 |
| Trp | Cys | Pro | Phe | Phe | Ile | Thr | Asn | Ile | Thr | Leu | Val | Leu | Cys | Asp | Ser | |
| | | | | 340 | | | | | 345 | | | | | 350 | | |
| TGT | AAC | CAA | ACT | ACT | CTC | CAA | ATG | CTC | CTG | GAG | ATA | TTT | GTG | TGG | ATA | 1104 |
| Cys | Asn | Gln | Thr | Thr | Leu | Gln | Met | Leu | Leu | Glu | Ile | Phe | Val | Trp | Ile | |
| | | | 355 | | | | | 360 | | | | | 365 | | | |
| GGC | TAT | GTT | TCC | TCA | GGA | GTG | AAT | CCT | TTG | GTC | TAC | ACC | CTC | TTC | AAT | 1152 |
| Gly | Tyr | Val | Ser | Ser | Gly | Val | Asn | Pro | Leu | Val | Tyr | Thr | Leu | Phe | Asn | |
| | 370 | | | | | 375 | | | | | 380 | | | | | |
| AAG | ACA | TTT | CGG | GAT | GCA | TTT | GGC | CGA | TAT | ATC | ACC | TGC | AAT | TAC | CGG | 1200 |
| Lys | Thr | Phe | Arg | Asp | Ala | Phe | Gly | Arg | Tyr | Ile | Thr | Cys | Asn | Tyr | Arg | |
| 385 | | | | | 390 | | | | | 395 | | | | | 400 | |
| GCC | ACA | AAG | TCA | GTA | AAA | ACT | CTC | AGA | AAA | CGC | TCC | AGT | AAG | ATC | TAC | 1248 |
| Ala | Thr | Lys | Ser | Val | Lys | Thr | Leu | Arg | Lys | Arg | Ser | Ser | Lys | Ile | Tyr | |
| | | | | 405 | | | | | 410 | | | | | 415 | | |
| TTC | CGG | AAT | CCA | ATG | GCA | GAG | AAC | TCT | AAG | TTT | TTC | AAG | AAA | CAT | GGA | 1296 |
| Phe | Arg | Asn | Pro | Met | Ala | Glu | Asn | Ser | Lys | Phe | Phe | Lys | Lys | His | Gly | |
| | | | 420 | | | | | 425 | | | | | 430 | | | |
| ATT | CGA | AAT | GGG | ATT | AAC | CCT | GCC | ATG | TAC | CAG | AGT | CCA | ATG | AGG | CTC | 1344 |
| Ile | Arg | Asn | Gly | Ile | Asn | Pro | Ala | Met | Tyr | Gln | Ser | Pro | Met | Arg | Leu | |
| | | 435 | | | | | 440 | | | | | 445 | | | | |
| CGA | AGT | TCA | ACC | ATT | CAG | TCT | TCA | TCA | ATC | ATT | CTA | CTA | GAT | ACG | CTT | 1392 |
| Arg | Ser | Ser | Thr | Ile | Gln | Ser | Ser | Ser | Ile | Ile | Leu | Leu | Asp | Thr | Leu | |
| | 450 | | | | | 455 | | | | | 460 | | | | | |
| CTC | CTC | ACT | GAA | AAT | GAA | GGT | GAC | AAA | ACT | GAA | GAG | CAA | GTT | AGT | TAT | 1440 |
| Leu | Leu | Thr | Glu | Asn | Glu | Gly | Asp | Lys | Thr | Glu | Glu | Gln | Val | Ser | Tyr | |
| 465 | | | | | 470 | | | | | 475 | | | | | 480 | |
| GTA | TAG | | | | | | | | | | | | | | | 1446 |
| Val | | | | | | | | | | | | | | | | |

( 2 ) INFORMATION FOR SEQ ID NO:2:

( i ) SEQUENCE CHARACTERISTICS:
    ( A ) LENGTH: 481 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

Met Ala Leu Ser Tyr Arg Val Ser Glu Leu Gln Ser Thr Ile Pro Glu

|     |     |     |     |     |     |     |     |     |     |     |     |     |     |     |
|---|---|---|---|---|---|---|---|---|---|---|---|---|---|---|
| 1 | | | | 5 | | | | | | 10 | | | | 15 |

His Ile Leu Gln Ser Thr Phe Val His Val Ile Ser Ser Asn Trp Ser
                20                      25                  30

Gly Leu Gln Thr Glu Ser Ile Pro Glu Glu Met Lys Gln Ile Val Glu
            35                  40              45

Glu Gln Gly Asn Lys Leu His Trp Ala Ala Leu Leu Ile Leu Met Val
        50                  55              60

Ile Ile Pro Thr Ile Gly Gly Asn Thr Leu Val Ile Leu Ala Val Ser
65                      70                  75                  80

Leu Glu Lys Lys Leu Gln Tyr Ala Thr Asn Tyr Phe Leu Met Ser Leu
                85                  90                  95

Ala Val Ala Asp Leu Leu Val Gly Leu Phe Val Met Pro Ile Ala Leu
            100                 105                 110

Leu Thr Ile Met Phe Glu Ala Met Trp Pro Leu Pro Leu Val Leu Cys
        115                 120             125

Pro Ala Trp Leu Phe Leu Asp Val Leu Phe Ser Thr Ala Ser Ile Met
    130                 135                 140

His Leu Cys Ala Ile Ser Val Asp Arg Tyr Ile Ala Ile Lys Lys Pro
145                 150                 155                 160

Ile Gln Ala Asn Gln Tyr Asn Ser Arg Ala Thr Ala Phe Ile Lys Ile
                165                 170                 175

Thr Val Val Trp Leu Ile Ser Ile Gly Ile Ala Ile Pro Val Pro Ile
            180                 185                 190

Lys Gly Ile Glu Thr Asp Val Asp Asn Pro Asn Asn Ile Thr Cys Val
            195                 200                 205

Leu Thr Lys Glu Arg Phe Gly Asp Phe Met Leu Phe Gly Ser Leu Ala
    210                 215                 220

Ala Phe Phe Thr Pro Leu Ala Ile Met Ile Val Thr Tyr Phe Leu Thr
225                 230                 235                 240

Ile His Ala Leu Gln Lys Lys Ala Tyr Leu Val Lys Asn Lys Pro Pro
                245                 250                 255

Gln Arg Leu Thr Trp Leu Thr Val Ser Thr Val Phe Gln Arg Asp Glu
            260                 265                 270

Thr Pro Cys Ser Ser Pro Glu Lys Val Ala Met Leu Asp Gly Ser Arg
        275                 280             285

Lys Asp Lys Ala Leu Pro Asn Ser Gly Asp Glu Thr Leu Met Arg Arg
    290                 295                 300

Thr Ser Thr Ile Gly Lys Lys Ser Val Gln Thr Ile Ser Asn Glu Gln
305                 310                 315                 320

Arg Ala Ser Lys Val Leu Gly Ile Val Phe Phe Leu Phe Leu Leu Met
                325                 330                 335

Trp Cys Pro Phe Phe Ile Thr Asn Ile Thr Leu Val Leu Cys Asp Ser
            340                 345                 350

Cys Asn Gln Thr Thr Leu Gln Met Leu Leu Glu Ile Phe Val Trp Ile
        355                 360             365

Gly Tyr Val Ser Ser Gly Val Asn Pro Leu Val Tyr Thr Leu Phe Asn
    370                 375                 380

Lys Thr Phe Arg Asp Ala Phe Gly Arg Tyr Ile Thr Cys Asn Tyr Arg
385                 390                 395                 400

Ala Thr Lys Ser Val Lys Thr Leu Arg Lys Arg Ser Ser Lys Ile Tyr
                405                 410                 415

Phe Arg Asn Pro Met Ala Glu Asn Ser Lys Phe Phe Lys Lys His Gly
            420                 425                 430

| Ile | Arg | Asn | Gly | Ile | Asn | Pro | Ala | Met | Tyr | Gln | Ser | Pro | Met | Arg | Leu |
| | | 435 | | | | 440 | | | | | 445 | | | | |

| Arg | Ser | Ser | Thr | Ile | Gln | Ser | Ser | Ser | Ile | Ile | Leu | Leu | Asp | Thr | Leu |
| | 450 | | | | 455 | | | | | 460 | | | | | |

| Leu | Leu | Thr | Glu | Asn | Glu | Gly | Asp | Lys | Thr | Glu | Glu | Gln | Val | Ser | Tyr |
| 465 | | | | 470 | | | | | 475 | | | | | 480 | |

Val ( 2 ) INFORMATION FOR SEQ ID NO:3:

( i ) SEQUENCE CHARACTERISTICS:
        ( A ) LENGTH: 1446 base pairs
        ( B ) TYPE: nucleic acid
        ( C ) STRANDEDNESS: single
        ( D ) TOPOLOGY: linear ( i i ) MOLECULE TYPE: mRNA ( x i ) SEQUENCE DESCRIPTION: SEQ ID NO:3:

```
AUGGCUCUCU CUUACAGAGU GUCUGAACUU CAAAGCACAA UUCCUGAGCA CAUUUUGCAG    60
AGCACCUUUG UUCACGUUAU CUCUUCUAAC UGGUCUGGAU UACAGACAGA AUCAAUACCA   120
GAGGAAAUGA AACAGAUUGU UGAGGAACAG GGAAAUAAAC UGCACGGGC AGCUCUUCUG   180
AUACUCAUGG UGAUAAUACC CACAAUUGGU GGAAAUACCC UUGUUAUUCU GGCUGUUUCA   240
CUGGAGAAGA AGCUGCAGUA UGCUACUAAU UACUUUCUAA UGUCCUUGGC GGUGGCUGAU   300
UUGCUGGUUG GAUUGUUUGU GAUGCCAAUU GCCCUCUUGA CAAUAAUGUU UGAGGCUAUG   360
UGGCCCCUCC CACUUGUUCU AUGUCCUGCC UGGUUAUUUC UUGACGUUCU CUUUCAACC   420
GCAUCCAUCA UGCAUCUCUG UGCCAUUUCA GUGGAUCGUU ACAUAGCCAU CAAAAAGCCA   480
AUCCAGGCCA AUCAAUAUAA CUCACGGGCU ACAGCAUUCA UCAAGAUUAC AGUGGUGUGG   540
UUAAUUUCAA UAGGCAUUGC CAUUCCAGUC CCUAUUAAAG GGAUAGAGAC UGAUGUGGAC   600
AACCCAAACA AUAUCACUUG UGUGCUGACA AAGGAACGUU UUGGCGAUUU CAUGCUCUUU   660
GGCUCACUGG CUGCCUUCUU CACACCUCUU GCAAUUAUGA UUGUCACCUA CUUUCUCACU   720
AUCCAUGCUU UACAGAAGAA GGCUUACUUA GUCAAAAACA AGCCACCUCA ACGCCUAACA   780
UGGUUGACUG UGUCUACAGU UUUCCAAAGG GAUGAAACAC CUUGCUCGUC ACCGGAAAAG   840
GUGGCAAUGC UGGAUGGUUC UCGAAAGGAC AAGGCUCUGC CAACUCAGG UGAUGAAACA   900
CUUAUGCGAA GAACAUCCAC AAUUGGGAAA AAGUCAGUGC AGACCAUUUC CAACGAACAG   960
AGAGCCUCAA AGGUCCUAGG GAUUGUGUUU UUCCUCUUUU UGCUUAUGUG GUGUCCCUUC  1020
UUUAUUACAA AUAUAACUUU AGUUUUAUGU GAUUCCUGUA ACCAAACUAC UCUCCAAAUG  1080
CUCCUGGAGA UAUUUGUGUG GAUAGGCUAU GUUUCCUCAG GAGUGAAUCC UUUGGUCUAC  1140
ACCCUCUUCA AUAAGACAUU UCGGGAUGCA UUUGGCCGAU AUAUCACCUG CAAUUACCGG  1200
GCCACAAAGU CAGUAAAAAC UCUCAGAAAA CGCUCCAGUA AGAUCUACUU CCGGAAUCCA  1260
AUGGCAGAGA ACUCUAAGUU UUUCAAGAAA CAUGGAAUUC GAAAUGGGAU UAACCCUGCC  1320
AUGUACCAGA GUCCAAUGAG GCUCCGAAGU UCAACCAUUC AGUCUUCAUC AAUCAUUCUA  1380
CUAGAUACGC UUCUCCUCAC UGAAAAUGAA GGUGACAAAA CUGAAGAGCA AGUUAGUUAU  1440
GUAUAG                                                             1446
```

( 2 ) INFORMATION FOR SEQ ID NO:4:

( i ) SEQUENCE CHARACTERISTICS:
        ( A ) LENGTH: 2238 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:4:

| | | | | | | |
|---|---|---|---|---|---|---|
| CCCACGCGTC | CGCAATGGGA | GGAGGATTTC | AGTCACAGCA | GCAAGCAAGT | CTAGTGAACA | 60 |
| GATAAGATGA | CATGCTCAGC | AAAATAACAA | CGAAACCAGA | GGGGGAACTC | TCTGGCATGC | 120 |
| AAGTTCAAAC | ACGACTCTAC | AACTACGGCA | GAAAAGAGA | GAGAGAGAAA | CTAAAAATAT | 180 |
| ATATATATCC | TATTTTTTTC | ACAGCTATCA | GTTTCTTTCA | CTGAGCTTTC | CTAAATTTAA | 240 |
| GCCTCTAGAA | AATAATAAAT | ACTTGGATAT | CTTACCTACA | AACATGGACA | GATGTGTGTA | 300 |
| TGCGCTCATT | TTAGAGAACT | TGAATTTTTT | TTTTAAAGG | AAGGTGTCAA | CTTTGGCTTT | 360 |
| TGAGTGTTTG | GCATGGTTAC | AATGCCTTAA | AAAAACAGAT | GAGCAGCTTA | GCTACTAACC | 420 |
| ATGCTGACCA | CTGTTCGGAA | CGGGATTGAA | TCACAGAAAA | ACAGCAAATG | GCTCTCTCTT | 480 |
| ACAGAGTGTC | TGAACTTCAA | AGCACAATTC | CTGAGCACAT | TTGCAGAGC | ACCTTTGTTC | 540 |
| ACGTTATCTC | TTCTAACTGG | TCTGGATTAC | AGACAGAATC | AATACCAGAG | GAAATGAAAC | 600 |
| AGATTGTTGA | GGAACAGGGA | AATAAACTGC | ACTGGGCAGC | TCTTCTGATA | CTCATGGTGA | 660 |
| TAATACCCAC | AATTGGTGGA | AATACCCTTG | TTATTCTGGC | TGTTTCACTG | GAGAAGAAGC | 720 |
| TGCAGTATGC | TACTAATTAC | TTTCTAATGT | CCTTGGCGGT | GGCTGATTTG | CTGGTTGGAT | 780 |
| TGTTTGTGAT | GCCAATTGCC | CTCTTGACAA | TAATGTTTGA | GGCTATGTGG | CCCCTCCCAC | 840 |
| TTGTTCTATG | TCCTGCCTGG | TTATTTCTTG | ACGTTCTCTT | TTCAACCGCA | TCCATCATGC | 900 |
| ATCTCTGTGC | CATTTCAGTG | GATCGTTACA | TAGCCATCAA | AAAGCCAATC | CAGGCCAATC | 960 |
| AATATAACTC | ACGGGCTACA | GCATTCATCA | AGATTACAGT | GGTGTGGTTA | ATTTCAATAG | 1020 |
| GCATTGCCAT | TCCAGTCCCT | ATTAAAGGGA | TAGAGACTGA | TGTGGACAAC | CCAAACAATA | 1080 |
| TCACTTGTGT | GCTGACAAAG | GAACGTTTTG | GCGATTCAT | GCTCTTTGGC | TCACTGGCTG | 1140 |
| CCTTCTTCAC | ACCTCTTGCA | ATTATGATTG | TCACCTACTT | TCTCACTATC | CATGCTTTAC | 1200 |
| AGAAGAAGGC | TTACTTAGTC | AAAAACAAGC | CACCTCAACG | CCTAACATGG | TTGACTGTGT | 1260 |
| CTACAGTTTT | CCAAAGGGAT | GAAACACCTT | GCTCGTCACC | GGAAAAGGTG | GCAATGCTGG | 1320 |
| ATGGTTCTCG | AAAGGACAAG | GCTCTGCCCA | ACTCAGGTGA | TGAAACACTT | ATGCGAAGAA | 1380 |
| CATCCACAAT | TGGGAAAAAG | TCAGTGCAGA | CCATTTCCAA | CGAACAGAGA | GCCTCAAAGG | 1440 |
| TCCTAGGGAT | TGTGTTTTTC | CTCTTTTTGC | TTATGTGGTG | TCCCTTCTTT | ATTACAAATA | 1500 |
| TAACTTTAGT | TTTATGTGAT | TCCTGTAACC | AAACTACTCT | CCAAATGCTC | CTGGAGATAT | 1560 |
| TTGTGTGGAT | AGGCTATGTT | TCCTCAGGAG | TGAATCCTTT | GGTCTACACC | CTCTTCAATA | 1620 |
| AGACATTTCG | GGATGCATTT | GGCCGATATA | TCACCTGCAA | TTACCGGGCC | ACAAAGTCAG | 1680 |
| TAAAAACTCT | CAGAAAACGC | TCCAGTAAGA | TCTACTTCCG | GAATCCAATG | GCAGAGAACT | 1740 |
| CTAAGTTTTT | CAAGAAACAT | GGAATTCGAA | ATGGATTAA | CCCTGCCATG | TACCAGAGTC | 1800 |
| CAATGAGGCT | CCGAAGTTCA | ACCATTCAGT | CTTCATCAAT | CATTCTACTA | GATACGCTTC | 1860 |
| TCCTCACTGA | AAATGAAGGT | GACAAAACTG | AAGAGCAAGT | TAGTTATGTA | TAGCTGAGAG | 1920 |
| CCAGTCAGTA | TGTATCGCAG | CACTGGCAGT | TGTCGTCAAA | CATAATGATG | AGTAAGATGA | 1980 |
| TGAATGAGAT | GTAAATGTGC | CAAGAATATA | TTATATAAAG | AATTTTATGT | CATATATCAA | 2040 |
| ATCATCTCTT | TAACCTAAGA | TGTAAGTATT | AAGAATATCT | AATTTTCCTA | ATTTGGACAA | 2100 |
| GATTATTCCA | TGAGGAAAAT | AATTTTATAT | AGCTACAAAT | GAAAACAATC | CAGCACTCTG | 2160 |

```
GTTAAATTTT   AAGGTATTCG   AATGAAATAA   AGTCAAATCA   ATAAATTTCA   GGCTTTAAAA      2220

AGAAAAAAAA   AAAAAAA                                                             2238
```